(12) United States Patent
Trauth et al.

(10) Patent No.: US 8,519,199 B2
(45) Date of Patent: *Aug. 27, 2013

(54) PROCESS FOR THE MANUFACTURE OF NITROPROPANES

(75) Inventors: Daniel M Trauth, Crystal Lake, IL (US); Richard L James, Eros, LA (US)

(73) Assignee: ANGUS Chemical Company

( * ) Notice: Subject to any disclaimer, the term of this patent is extended or adjusted under 35 U.S.C. 154(b) by 75 days.

This patent is subject to a terminal disclaimer.

(21) Appl. No.: 12/934,810

(22) PCT Filed: Apr. 8, 2009

(86) PCT No.: PCT/US2009/039906
§ 371 (c)(1),
(2), (4) Date: Sep. 27, 2010

(87) PCT Pub. No.: WO2009/129099
PCT Pub. Date: Oct. 22, 2009

(65) Prior Publication Data
US 2011/0028731 A1 Feb. 3, 2011

Related U.S. Application Data

(60) Provisional application No. 61/045,378, filed on Apr. 16, 2008.

(51) Int. Cl.
C07C 201/16 (2006.01)

(52) U.S. Cl.
USPC .......................................... 568/944; 568/704

(58) Field of Classification Search
USPC ................................. 568/944, 704; 564/495
See application file for complete search history.

(56) References Cited

U.S. PATENT DOCUMENTS

| | | |
|---|---|---|
| 1,967,667 A | 10/1933 | Hass et al. |
| 2,139,121 A | 12/1938 | Hass et al. |
| 2,139,124 A | 12/1938 | Hass et al. |
| 2,489,320 A | 11/1945 | Nygaard et al. |
| 2,511,454 A | 3/1950 | Evans et al. |
| 3,066,173 A | 12/1962 | Lee et al. |
| 3,272,874 A | 9/1966 | Abbott et al. |
| 3,564,057 A | 2/1971 | Tindall et al. |
| 3,780,115 A | 12/1973 | Lhonore et al. |
| 3,869,253 A | 3/1975 | Lhonore et al. |
| 3,962,271 A | 6/1976 | Sidi et al. |
| 4,304,942 A | 12/1981 | Ho |
| 4,329,523 A | 5/1982 | James et al. |
| 4,518,811 A | 5/1985 | Lhonore et al. |
| 4,861,925 A | 8/1989 | Quirk |
| 5,288,907 A | 2/1994 | Sherwin et al. |
| 5,604,229 A | 2/1997 | Fijita et al. |
| 6,072,063 A | 6/2000 | Eyrisch et al. |
| 6,279,656 B1 | 8/2001 | Sinclair et al. |
| 2004/0152749 A1 | 8/2004 | Merianos et al. |
| 2011/0028732 A1 | 2/2011 | Trauth et al. |
| 2011/0092737 A1* | 4/2011 | Trauth ........................ 564/301 |
| 2011/0092748 A1* | 4/2011 | Sawant et al. ................ 568/944 |
| 2011/0092750 A1 | 4/2011 | Trauth et al. |

FOREIGN PATENT DOCUMENTS

| | | |
|---|---|---|
| BE | 621923 | 10/1961 |
| DE | 19527121 | 1/1997 |
| EP | 2019100 | 1/2009 |
| GB | 1245469 | 9/1971 |
| WO | 0042079 A1 | 7/2000 |

OTHER PUBLICATIONS

Albright, "Nitration of Paraffins", Chemical Engineering, 1966, pp. 149-156.
Asinger et al., "Question of isomer formation during nitration of simple and substituted paraffinic hydrocarbons", Chem. Ber. 1967, vol. 100 No. 2, pp. 438-447.
Dell'Erba et al., "Synthetic Exploitation of the Ring-Opening of 3,4-Dinitrothiophene. Part 3. Access to 1,4-Diaryl- and 1,4-Dialkyl-2-nitrobutanes", Tetrahedron Letters, 1992, vol. 33 No. 46, pp. 7047-7048.
Geiseler, "Nitration of Saturated Hydrocarbons with Nitrogen Dioxide in the Liquid Phase", Angew. Chem., 1955, 9, p. 270-273.
Geiseler et al.,"On the nitration of iso-octane with nitrogen dioxide", Z. Chem. 1962, vol. 2 No. 10, p. 311.
Ghidini et al., "Synthesis of a new series of N-hydroxy, N-alkylamides of aminoacids as ligands of NMDA glycine site", European Journal of Medicinal Chemistry, 1999, vol. 34 No. 9, pp. 711-717.
Kornblum et al., "The Reaction of Silver Nitrite with Primary Alkyl Halides", Journal of the American Chemical Society, 1954, vol. 76, pp. 3209-3211.
Larock, "Comprehensive Organic Transformations: A Guide to Functional Group Preparations", VCH Publishers, 1989, pp. 411-415.
Nakahara et al., "Vapor-phase nitration of propane with nitric acid", Database Caplus, Chemical Abstracts Service, 1979.
Nishiwaki et al., "An Efficient Nitration of Light Alkanes and the Alkyl Side-Chain of Aromatic Compounds with Nitrogen Dioxide and Nitric Acid Catalyzed by N-Hydroxyphthalimide", Journal of Organic Chemistry, 2002, vol. 67 No. 16, pp. 5663-5668, American Chemical Society.
Noland et al., "Heterocyclic Spiranes Oxazolidines from (1-Aminocyclohexyl)methanol", Journal of Organic Chemistry, 1960, vol. 25, pp. 1155-1159.
Rosini et al., "Functionalized Nitroalkanes as Useful Reagents for Alkyl Anion Synthons", Synthesis, 1988, pp. 833-847.
Ryer et al., "Reactions of N-Monoalkylhydroxylamines with Sulfur Dioxide, Sulfur Trioxide and Phthalic Anhydride", Journal of the American Chemical Society, 1951, vol. 73 No. 12, pp. 5675-5678.
Wheatley, "Alpha, alpha-Dimethylcholine: Esters and Carbamates", Journal of the American Chemical Society, 1954, vol. 76, pp. 2832-2835.
"Alkanolamines" Kirk-Othmer Concise Encyclopedia of Chemical Technology, 1985, pp. 67-69.
"Nitro Alcohols", Kirk-Othmer Concise Encyclopedia of Chemical Technology, 1985, pp. 789-790.
International Search Report and Written Opinion for PCT/US2009/039901 dated Aug. 19, 2009.

* cited by examiner

Primary Examiner — Kristin Vajda

(57) ABSTRACT

Provided is a process for the formation of 2-nitropropane and/or 2,2-dinitropropane by the nitration of propane with dilute nitric acid.

10 Claims, No Drawings

PROCESS FOR THE MANUFACTURE OF NITROPROPANES

CROSS-REFERENCE TO RELATED APPLICATIONS

This is a §371 application of PCT International Patent Application No. PCT/US2009/039906 filed Apr. 8, 2009, and claims the benefit of U.S. Provisional Application No. 61/045,378, filed Apr. 16, 2008, each of which is incorporated herein by reference in its entirety.

FIELD OF THE INVENTION

The invention relates to a process for making nitropropanes, such as 2-nitropropane and 2,2-dinitropropane. More specifically, the process comprises reacting aqueous nitric acid with propane under specific reaction conditions.

BACKGROUND OF THE INVENTION

The nitration of hydrocarbons generally produces a variety of products depending upon the reaction conditions and the feedstock structure. For instance, the commercial vapor phase process for propane nitration results in a mixture of four nitroparaffin products (nitromethane, 1-nitropropane, 2-nitropropane, and nitroethane) in essentially fixed relative concentrations.

Certain products, however, may be more desirable than others and it has been a long-time goal to selectively produce the more useful nitrated compounds at the expense of the less useful compounds. In contrast to commercial vapor phase nitration, the mixed vapor-liquid phase or high pressure nitration of propane has been postulated in the past to be a technique by which 2-nitropropane, a more desirable nitroparaffin, can be potentially produced without making the other nitro compounds typically formed during vapor-phase nitration. See e.g., U.S. Pat. No. 2,489,320 (Nygaard et al.) and Albright, L. F., "Nitration of Paraffins", Chem. Engr., (1966) pp. 149-156.

The prior art technology for nitrating propane in the mixed vapor-liquid phase was never practical for a number of reasons, including because the conversion of nitric acid is low, the nitric acid is not readily recoverable, problems with reactor corrosion by the nitric acid, and difficulty in controlling reaction exotherm.

Obtaining a high yield of a selectively nitrated hydrocarbon is a critical economic factor to be considered since low yields necessitate the use of more feed and therefore result in higher costs. Furthermore, when nitric acid is used as the nitrating agent, the unreacted nitric acid becomes a waste product and costs are incurred to dispose of waste products properly. High conversion of the reactant hydrocarbon is also economically critical in order to minimize capital and energy expenses associated with the purification and recycling of unreacted reactants. A need exists, therefore, for more economical, selective, and environmentally friendly processes for the manufacture of selectively nitrated nitroparaffins.

BRIEF SUMMARY OF THE INVENTION

In one aspect, the invention provides a process for the selective nitration of propane. The process of the invention avoids the practical problems encountered in the past, such as low yields, conversions, and excess waste production. The process comprises: reacting propane with aqueous nitric acid at a pressure of at least about 1000 psi and a temperature of between about 215 and about 325 degrees Celsius; and recovering the formed nitrated compounds, wherein the aqueous nitric acid is a 20 to 40 weight percent solution.

In another aspect the invention provides a product stream from a nitroparaffin nitration process that contains a 2-nitropropane to 2,2-dinitropropane weight ratio of at least about 15:1.

DETAILED DESCRIPTION OF THE INVENTION

As noted above, in one aspect the invention provides a process for the nitration of propane with nitric acid. Use of the reaction conditions described herein, including in particular the reaction temperature and the concentration of nitric acid in the aqueous acid solution, provides a nitration process that is significantly improved over prior art processes.

One important advantage of the process of the invention is that it provides increased conversion of nitric acid to desired product. Thus, in some embodiments, the invention is capable of converting at least 15 mol %, preferably at least 20 mol %, more preferably at least 25 mol %, and even more preferably at least 30 mol %, of the nitric acid to 2-nitropropane and/or 2,2-dinitropropane (calculated as moles of nitric acid fed divided by total moles of 2-nitropropane and 2,2-dinitropropane formed). In contrast, the maximum conversion of nitric acid to 2-nitropropane and 2,2-dinitropropane described, for example, in the prior art process of U.S. Pat. No. 2,489,320 is 12 percent (see example 1 thereof).

In addition to this improved conversion to desired product, in some embodiments the invention also allows at least 95% of the nitric acid to be consumed (determined as follows: (nitric acid in—nitric acid out)/nitric acid in). The converted nitric acid that does not result in nitroparaffins is in the readily recovered form of nitric oxide (NO).

Another important advantage of the process of the invention is that it provides increased hydrocarbon feedstock conversion to desired product than obtainable with prior art systems. Thus, in some embodiments, the invention is capable of converting at least about 10 mol %, preferably at least about 15 mol %, more preferably at least about 20 mol %, of starting propane to 2-nitropropane and/or 2,2-dinitropropane product (determined by dividing the number of moles of 2-nitropropane and 2,2-dinitropropane formed by the number of moles of propane that is fed into the reaction). In contrast, the conversion of propane to 2-nitropropane and 2,2-dinitropropane in, for instance, example 1 of the prior art process of U.S. Pat. No. 2,489,320 is only 6.2 mol %.

A further important aspect of the process of the invention, as compared to commercially practiced processes, is the reduced amount of nitromethane that is generated as a by-product. Nitromethane is a detonable liquid compound that requires additional equipment for safe handling. Thus its reduction is a highly desirable feature of any commercial nitration process. In some embodiments, the process of the invention is capable of providing desired nitration products containing 3 weight percent or less, more preferably 1.5 weight percent or less, of nitromethane as a by-product. The low level of nitromethane with the invention means that the nitromethane can be removed as part of a waste stream, rather than requiring special handling and equipment. In contrast, nitromethane concentration in commercial processes for nitration of propane can be about 25 weight percent (based on the percentage by weight of nitromethane compared to the total weight of nitromethane, nitroethane, 1-nitropropane and 2-nitropropane, the four primary products of commercial processes).

Aldehydes are another by-product in nitration processes. When present in sufficient quantities, aldehydes render the aqueous waste product untreatable by biotreatment techniques, instead requiring the use of aldehyde abatement equipment. Such equipment can add to the complexity and expense of the nitration process. It is highly desirable, therefore, that the concentration of aldehydes in waste streams be reduced. As demonstrated by Example 3, the waste stream in the inventive process is capable of containing sufficiently low levels of aldehyde that biotreatment is a viable treatment option. In contrast, biotreatment is not generally an option with commercial processes which instead require hazardous-waste deep well disposal.

According to the first aspect of the invention, propane is nitrated with aqueous nitric acid to form 2-nitropropane and other nitrated paraffins under the specific process conditions described herein. Advantageously, the reaction of propane with nitric acid is carried out in a corrosion resistant reactor, such as a titanium reactor. The reactor is optionally surrounded by a shell with input and output ports for feeding a heat transfer fluid to the reactor. The heat transfer fluid, which can be, for example, an oil, allows the temperature of the reaction to be controlled to within the desired parameters.

It should be noted, however, that because the reaction between the nitric acid and propane is exothermic, use of a shell and a heat transfer fluid are not required. The temperature of the reaction can be regulated to be within the desired parameters by simply regulating the addition rate and/or concentration of the reactants.

In a preferred embodiment of the invention, the reactor is operated in a downflow mode. That is, the reactor, which is preferably of an elongated and linear shape, such as a tube shape, is positioned so that reactants are added through an entry port at or near the top of the reactor and then flowed down the reactor for sufficient residence time to allow reaction to occur and formation of the desired product. The product mixture is collected through an exit port at or near the bottom of the reactor.

The operation of the reactor in a downflow configuration provides certain advantages over prior art systems, which generally utilize a horizontal, upflow, coiled or a batch autoclave type apparatus. In particular, the downflow configuration of the invention provides nitrated compounds that contain relatively low levels of oxidation byproducts as compared to such prior art systems.

Without wishing to be bound by any particular theory, it is believed that the advantages of the downflow reactor result primarily from its ability to minimize the amount and residence time of the liquid phase within the reactor. The liquid phase in general contains a low mole ratio of hydrocarbons to nitric acid. This low mole ratio favors oxidation chemistry at the expense of nitration and oxidation therefore primarily occurs in the liquid phase. In a downflow reactor (also referred to as a trickle bed reactor) the gas is the continuous phase and the liquid trickles down the reactor walls or packing. Therefore, the amount of liquid phase(s) in a downflow configured reactor is maintained at a low level and consequently oxidation chemistry is minimized.

In contrast, in an upflow reactor, also referred to as a bubble column, the liquid is the continuous phase (and bubbles rise quickly through the continuous liquid phase). Thus, an upflow reactor maximizes the liquid holdup. Because, as noted above, oxidation primarily occurs in the liquid phase, the upflow reactor maximizes the formation of oxidation byproducts. Similarly, coil and horizontal reactor configurations also increases liquid residence time and therefore oxidation chemistry as compared to a downflow reactor. A further disadvantage of coiled reactors is that they are not well-suited for industrial scale production because of the difficulty of fabricating large scale reactors in this shape.

The reactor is optionally packed with a packing material to improve reactant mixing and heat transfer and/or to vary the reactor volume. Packing of the reactor is particularly preferred where it is desired to increase the concentration of 2,2-dinitropropane in the product stream. Suitable packing materials include, for example, glass beads, random packing, or structured packing, such as those typically employed in distillation devices. Other packing materials are known in the art and may be used.

The propane and nitric acid can be mixed, or partially mixed, prior to entry into the reactor or, alternatively, they can be added individually, with mixing to occur within the reactor. Further, the reactants, whether added together or individually, can be preheated prior to entry into the reactor.

The nitric acid is delivered to the reactor in the form of an aqueous solution that contains at least about 10 weight percent, preferably at least about 15 weight percent, more preferably at least about 20 weight percent, of the acid. Further, the solution contains no more than about 50 weight percent, preferably no more than about 40 weight percent, and more preferably no more than about 35 weight percent, of the acid. In further embodiments, the nitric acid solution contains between about 15 and about 40 weight percent of the acid. In other embodiments, the nitric acid solution contains between about 18 and about 35 weight of the acid.

The mole ratio of propane to nitric acid should be at least about 1:1, more preferably at least about 1.2:1.

The reaction temperature within the reactor is generally controlled (for example with heat exchange fluid or using heat generated from the reaction, as described above) to at least about 215 degrees Celsius and to no more than about 325 degrees Celsius. In some embodiments, the temperature is at least about 220 degrees, at least about 230 degrees or at least about 240 degrees. In further embodiments, the temperature is no more than about 290 degrees, no more than about 280 degrees, or no more than about 270 degrees. In other embodiments, the temperature is between about 215 and 280 degrees Celsius, or between about 220 and 270 degrees Celsius.

The pressure in the reactor should be maintained at least about 1000 psi (68 atm), preferably at least about 1200 psi (82 atm). Further preferably, the pressure is about 1600 psi (109 atm) or less, preferably about 1500 psi (102 atm) or less, more preferably about 1400 psi (95 atm) or less. In further embodiments, the pressure is between about 1200 psi (82 atm) and 1400 psi (95 atm). Various methods known in the art can be used for maintaining the pressure within the desired range including, for example, through the use of a back-pressure regulator.

The residence time of the reactants in the reactor is preferably at least about 30 seconds, more preferably at least about 90 seconds. Residence time can be controlled in various ways including, for example, by the length and/or width of the reactor or through the use of packing material. Residence time is determined by dividing the volume of the reactor by the inlet flow rates.

Following sufficient residence time, the nitration products are collected from the reactor through the reactor's exit port. Further processing, such as distillation, may be carried out on the nitration products to, for example, isolate or purify the particularly desirable materials, such as the 2-nitropropane and/or 2,2-dinitropropane.

While 2,2-dinitropropane is a useful product of the nitration reaction of the invention, in some embodiments it is desirable to produce a nitroparaffin stream that is enriched in 2-nitropropane. Accordingly, in a further aspect, the invention provides a product stream, in particular the organic portion thereof, that is the direct product of a nitration process (i.e., without further purification to enrich particular nitroparaffin components). The product stream comprises 2-nitropropane; nitromethane; nitroethane; 1-nitropropane; and 2,2-dinitropropane. The weight ratio of 2-nitropropane to 2,2-dinitropropane in the stream is at least about 15:1, preferably at least about 30:1, more preferably at least about 40:1, further preferably at least about 50:1, and even more preferably at least about 60:1.

The 2-nitropropane prepared according to the invention can be used for making a variety of downstream, industrially useful, products including, for example, 2-nitro-2-methyl-1-propanol (NMP), 2-amino-2-methyl-1-propanol (AMP), 2-dimethylamino-2-methyl-1-propanol (DMAMP), N-isopropylhydroxylamine (IPHA), and 4,4-dimethyl-1,3-oxazolidine. Preparation of these materials from the starting 2-nitropropane is accomplished through techniques well known to those skilled in the art.

For example, 2-nitro-2-methyl-1-propanol (NMP) can be obtained by the addition reaction of 2-nitropropane (2-NP) and formaldehyde in the presence of an alkaline catalyst, such as sodium hydroxide or trimethylamine. See for example GB 1245469. Typically the reaction involves batchwise or continuously reacting 2-nitropropane with an aqueous solution of formaldehyde at a mole ratio of about 1:1 2-NP to formaldehyde and at a temperature of approximately 70-80° C. The catalyst is used in an amount sufficient to provide a normality of 0.01-0.05 in the reaction mixture. Typically, the reaction is conducted without solvent. The product can typically be used directly as the aqueous solution or crystallized from the aqueous solution or recovered as a cast solid by stripping off solvents under vacuum and freezing the liquid NMP in pans or other containers.

NMP can be reduced to 2-amino-2-methyl-1-propanol via hydrogenation in the presence of Raney nickel (see "Nitro Alcohols" Kirk-Othmer Concise Encyclopedia of Chemical Technology, 1985, pp 789-790, and U.S. Pat. No. 3,564,057, each incorporated herein by reference). Typically the hydrogenation is conducted in an aqueous methanol or ethanol solution at a temperature of about 70-100° C. and a pressure of 400-600 p.s.i.g. The Raney nickel catalyst is used in a concentration of between about 2 and 10 weight percent of the NMP to be hydrogenated. The product can be readily recovered through filtration of catalyst, followed by distillation of first solvents, then the AMP product.

N-isopropylhydroxylamine can be prepared via hydrogenation of 2-nitropropane in the presence of a palladium catalyst (such as $Pd/Al_2O_3$), for instance according to U.S. Pat. No. 5,288,907 which is incorporated herein by reference. Typically the hydrogenation is carried out in water or methanol at 50-75° C. and 30-600 p.s.i.g. $H_2$, with good agitation for 4-6 hours. The product is typically recovered by filtering off the catalyst, then storing, and using directly as an aqueous solution due to the lower thermal stability of the concentrated free hydroxylamine.

2-Dimethylamino-2-methyl-1-propanol is manufactured from AMP by hydrogenation in the presence of formaldehyde and purified by distillation (see "Alkanolamines" Kirk-Othmer Concise Encyclopedia of Chemical Technology, 1985, pp 68-69, incorporated by reference). Typically, the reaction is conducted in methanol solvent, with 2-3 molar equivalents of formaldehyde for each mole of AMP. The reactants are heated with good agitation at 100-160° C. for 4-6 hours at 400-700 psig hydrogen pressure. The DMAMP product can be readily recovered by filtration of catalyst followed by first distilling off solvents, then distilling the product itself.

4,4-Dimethyl oxazolidine may be produced by the reaction of equimolar amounts of formaldehyde and 2-amino-2-methyl-1-propanol (see for example BE 621923). Typically, the reaction is conducted without solvent at about 50-70° C. temperature for a period of 1-2 hours. The product can be directly packaged and used without additional processing as the aqueous solution obtained from the condensation reaction.

The following examples are illustrative of the invention but are not intended to limit its scope.

EXAMPLES

General. Various aspects of the invention are demonstrated using a lab scale reactor. The reactor is a single tube shell-and-tube heat exchanger with a thermowell located axially down the center of the reactor in order to determine the temperature profile along the reactor's length. The reactor is 46" long and has a shell which is 1.25" OD 304 stainless steel with a ½" OD (0.37" ID) type 2 titanium process tubing and a ⅛" OD (0.093" ID) type 2 titanium thermowell. A very fine, movable thermocouple is inserted into the thermowell for the temperature profile measurement. The thermowell can be removed and the reactor filled with packing. The reactor is mounted vertically. The nitric acid and propane reactant streams are mixed in a Swagelok "T" at room temperature prior to entering the reactor. Hot oil used is fed to the reactor shell countercurrent to the reactants. The reactor effluent is cooled in a shell-and-tube heat exchanger using city water as the coolant. The effluent is then depressurized with the gases and liquids collected, measured, and analyzed.

In the examples below, the mass balance of the nitration reaction is determined by GC/MS for gases, aqueous, nitroparaffin oil, and scrubber liquids, Karl Fisher titration for water content, potentiometric titration for strong/weak acid quantification, and HPLC for weak acid identification and quantification.

Metrics shown in the Tables below are calculated as follows:

Grams of nitric acid consumed is calculated by subtracting the moles of NO in the effluent from the moles of nitric acid in the feed then converting the number of moles to grams using the molecular weight of nitric acid. This accounts for the recovery of NO in the off-gas as nitric acid;

Grams nitroparaffins formed=g of nitromethane+g nitroethane+g 1-nitropropane+g 2-nitropropane+g 2,2 dinitropropane;

Nitric Acid Yield=grams nitric acid consumed/g nitroparaffins formed;

Propane Yield=grams propane consumed/g nitroparaffins formed;

Nitric Acid conversion (%)=100×(Nitric Acid in−Nitric Acid out)/Nitric Acid in;

Propane conversion (%)=100×(Propane in−Propane out)/Propane in;

2-nitropropane selectivity (%)=100×g 2-nitropropane/g nitroparaffins formed;

2,2 dinitropropane selectivity (%)=100×g 2,2 dinitropropane/g nitroparaffins formed;

Acetic acid formed: g acetic acid formed/g nitroparaffins formed.

Example 1

Nitration of Propane with Dilute Nitric Acid; 255° C. Hot Oil Temperature

Propane is nitrated using dilute aqueous nitric acid as the nitrating agent with the above-described reactor at the following process conditions: 1400 psi reactor pressure, 255° C. hot oil temperature, 1.4:1 propane to nitric acid mole ratio, 25.5 wt. % nitric acid strength (in water), and 120 second residence time (based on the volume of the reactor divided by the flow rate of the feeds at room temperature and 1400 psi). The reactor was not packed. The results of the mass balance are shown in Table 1:

TABLE 1

| Component | Feed (g) | Effluent (g) |
|---|---|---|
| Propane | 483 | 268 |
| Nitric Acid | 489 | 18.8 |
| Water[1] | 2679 | 2966 |
| Acetic Acid | 0 | 65.8 |
| Acetone | 0 | 2.9 |
| Nitromethane | 0 | 4.6 |
| Nitroethane | 0 | 2.4 |
| 2-Nitropropane | 0 | 234 |
| 1-Nitropropane | 0 | 32.5 |
| 2,2-Dinitropropane | 0 | 3.8 |
| Nitric Oxide | 0 | 94.4 |
| Nitrous Oxide | 0 | 12.7 |
| Nitrogen | 0 | 13.9 |
| Carbon Monoxide | 0 | 21.6 |
| Carbon Dioxide | 0 | 49.3 |

[1]Water in versus water out includes water used to scrub the off-gas from the reactor.

Key performance metrics of the reaction are provided in Table 2.

TABLE 2

| | |
|---|---|
| Nitric Acid Conversion | 96.2 |
| Propane Conversion | 44.5 |
| Nitric Acid Yield | 0.98 |
| Propane Yield | 0.78 |
| 2-nitropropane selectivity | 84.4 |

These results demonstrate the high conversion and yields of the reactants to the desired product, 2-nitropropane. It should be understood that these results are for a single pass reactor. In the full scale process, most of the unreacted nitric acid would be recycled to dilute the fresh nitric acid feed, leading to overall nitric acid conversion of approximately 99%.

Efficient raw material conversion to desired product is a critical key requirement for a commercial scale production of nitropropane, and is a significant advantage of the invention. Conversion is measured in terms of a combination of conversion and raw material yields. The data is provided in Table 3. As can be seen, the results from the example of the invention are approximately three times higher than reported in U.S. Pat. No. 2,489,320.

TABLE 3

| | U.S. Pat. No. 2,489,320 | Current |
|---|---|---|
| Weight ratio of nitropropanes formed/nitric acid fed | 0.188 | 0.553 |
| Weight ratio of nitropropanes formed/propane fed | 0.152 | 0.560 |

Note:
In Table 3, nitropropanes formed includes 1-nitropropane, 2-nitropropane, and 2,2-dinitropropane.

Example 2

Nitration of Propane; 235° C. Hot Oil Temperature

Propane is nitrated using dilute aqueous nitric acid as the nitrating agent with the above-described reactor at the following process conditions: 1400 psi reactor pressure, 235° C. hot oil temperature, 1.35:1 propane to nitric acid mole ratio, 29.8 wt. % nitric acid strength (in water), and 120 second residence time (based on the volume of the reactor divided by the flow rate of the feeds at room temperature and 1400 psi). The reactor was not packed. The results of the mass balance are shown in Table 4:

TABLE 4

| Component | Feed (g) | Effluent (g) |
|---|---|---|
| Propane | 570 | 339 |
| Nitric Acid | 604 | 73.4 |
| Water[1] | 2538 | 2768 |
| Acetic Acid | 0 | 73.6 |
| Acetone | 0 | 1.8 |
| Nitromethane | 0 | 4.1 |
| Nitroethane | 0 | 2.0 |
| 2-Nitropropane | 0 | 221 |
| 1-Nitropropane | 0 | 33.9 |
| 2,2-Dinitropropane | 0 | 3.7 |
| Nitric Oxide | 0 | 123 |
| Nitrous Oxide | 0 | 12.1 |
| Nitrogen | 0 | 14.5 |
| Carbon Monoxide | 0 | 23.4 |
| Carbon Dioxide | 0 | 56.7 |

[1]Water in versus water out includes water used to scrub the off-gas from the reactor.

Key performance metrics of the reaction are provided in Table 5.

TABLE 5

| | |
|---|---|
| Nitric Acid Conversion | 87.9 |
| Propane Conversion | 40.6 |
| Nitric Acid Yield | 1.31 |
| Propane Yield | 0.88 |
| 2-nitropropane selectivity | 83.5 |

These results demonstrate the high conversion and yields of the reactants to the desired product, 2-nitropropane.

Efficient raw material conversion to desired product is a critical key requirement for a commercial scale production of nitropropane, and is a significant advantage of the invention. Conversion is measured in terms of a combination of conversion and raw material yields. The data is provided in Table 6. As can be seen, the results from the example of the invention are approximately three times higher than reported in U.S. Pat. No. 2,489,320.

TABLE 6

| | U.S. Pat. No. 2,489,320 | Current |
|---|---|---|
| Weight ratio of nitropropanes formed/nitric acid fed | 0.188 | 0.428 |
| Weight ratio of nitropropanes formed/propane fed | 0.152 | 0.454 |

Example 3

Nitration of Propane; 285° C. Hot Oil Temperature

Propane is nitrated using dilute aqueous nitric acid as the nitrating agent with the above-described reactor at the following process conditions: 1400 psi reactor pressure, 285° C. hot oil temperature, 1.21:1 propane to nitric acid mole ratio, 20.0 wt. % nitric acid strength (in water), and 75 second residence time (based on the volume of the reactor divided by the flow rate of the feeds at room temperature and 1400 psi). The reactor was not packed. The results of the mass balance are shown in Table 7:

TABLE 7

| Component | Feed (g) | Effluent (g) |
|---|---|---|
| Propane | 191 | 92.4 |
| Nitric Acid | 226 | 13.8 |
| Water | 905 | 1029 |
| Acetic Acid | 0 | 29.4 |
| Acetone | 0 | 9.6 |
| Nitromethane | 0 | 1.9 |
| Nitroethane | 0 | 1.3 |
| 2-Nitropropane | 0 | 127 |
| 1-Nitropropane | 0 | 12.4 |
| 2,2-Dinitropropane | 0 | 2.1 |
| Nitric Oxide | 0 | 32.8 |
| Nitrous Oxide | 0 | 4.0 |
| Nitrogen | 0 | 0.3 |
| Carbon Monoxide | 0 | 7.7 |
| Carbon Dioxide | 0 | 16.9 |

Key performance metrics of the reaction are provided in Table 8.

TABLE 8

| Nitric Acid Conversion | 93.9 |
|---|---|
| Propane Conversion | 51.5 |
| Nitric Acid Yield | 1.09 |
| Propane Yield | 0.68 |
| 2-nitropropane selectivity | 87.7 |

These results demonstrate the high conversion and yields of the reactants to the desired product, 2-nitropropane.

Efficient raw material conversion to desired product is a critical key requirement for a commercial scale production of nitropropane, and is a significant advantage of the invention. Conversion is measured in terms of a combination of conversion and raw material yields. The data is provided in Table 9. As can be seen, the results from the example of the invention are approximately three times higher than reported in U.S. Pat. No. 2,489,320.

TABLE 9

| | U.S. Pat. No. 2,489,320 | Current |
|---|---|---|
| Weight ratio of nitropropanes formed/nitric acid fed | 0.188 | 0.626 |
| Weight ratio of nitropropanes formed/propane fed | 0.152 | 0.743 |

Example 4

Comparison of Biotreatability of Wastewater

A 49 day long continuous biotreatment test (set up as a two-stage anoxic/aerobic reactor system) of the product stream from example 2, distilled to remove soluble nitroparaffins, is conducted. The biotreatment test demonstrates 99.7% nitrate removal and 99.4% COD (chemical-oxygen demand) removal indicating excellent treatability. No indications of toxicity are noted in carbonaceous bioconversion or denitrification/nitrification reactions.

Biotreatment is not practical with the waste stream from the commercial process primarily because of the presence of large amounts of aldehydes. Deepwell disposal is used with commercial processes.

Example 5

Effect of Internal Reactor Temperature on Nitromethane Concentration

The 4 runs shown in the Table 10 are completed using the lab reactor at the following process conditions: 1400 psig, residence time ranged from 106 to 121 seconds, propane to nitric acid mole ratio ranged from 3:1 to 4:1. (Note, the propane to nitric acid mole ratio is higher than optimal in order to try and use unreacted propane as a heat sink when higher strength nitric acid was used—it had only a minuscule effect).

TABLE 10

| Run | Nitric Acid Strength (wt. %) | Hot Oil Temperature (C.) | Peak Internal Reactor Temperature (C.) | Difference Between Peak Internal Temperature and Hot Oil | NM (wt %) |
|---|---|---|---|---|---|
| A | 47 | 230 | 333 | 103 | 5.6 |
| B | 40 | 240 | 287 | 47 | 2.2 |
| C | 35 | 235 | 272 | 37 | 0.6 |
| D | 20 | 240 | 242 | 2 | 0.8 |

Note:
In Table 10, NM (wt. %) refers to the weight percent of nitromethane in the liquid oil phase.

Higher strength nitric acid leads to a bigger hot spot in the reactor. The effect of a hotter maximum internal reactor temperature is increased nitromethane formation.

Example 6

Control of 2,2 DNP Production using Packing

Example 1 in this application showed a low level of 2,2 DNP in the reactor effluent. The amount of 2,2 DNP may be increased by adding packing to the reactor.

Propane is nitrated using dilute aqueous nitric acid as the nitrating agent using the above-described reactor at the following process conditions: 1400 psi reactor pressure, 235° C. hot oil temperature, 1.8:1 propane to nitric acid mole ratio, 30.9 wt. % nitric acid strength (in water), and 120 second residence time (based on the volume of the reactor divided by the flowrates of the feeds at room temperature and 1400 psi). In this case the reactor is packed with 3 mm borosilicate glass balls prior to running the experiment. The results of the mass balance for this example are shown in Table 11.

TABLE 11

| Component | Feed (g) | Effluent (g) |
|---|---|---|
| Propane | 448 | 334 |
| Nitric Acid | 362 | 5.9 |
| Water | 2086 | 2225 |
| Acetic Acid | 0 | 49.4 |
| Acetone | 0 | 1.0 |
| Nitromethane | 0 | 0.5 |
| Nitroethane | 0 | 0.3 |
| 2-Nitropropane | 0 | 88.5 |
| 1-Nitropropane | 0 | 10.6 |
| 2,2-Dinitropropane | 0 | 7.1 |
| Nitric Oxide | 0 | 68.7 |
| Nitrous Oxide | 0 | 14.9 |
| Nitrogen | 0 | 13.8 |
| Carbon Monoxide | 0 | 16.6 |
| Carbon Dioxide | 0 | 47.8 |

Key performance metrics are shown in Table 12.

TABLE 12

| Nitric Acid Conversion | 98.4 |
|---|---|
| Propane Conversion | 25.3 |
| Nitric Acid Yield | 1.98 |
| Propane Yield | 1.07 |
| 2-nitropropane selectivity | 82.7 |

Comparison of 2,2 DNP selectivity between Example 1 and this example is shown in Table 13.

TABLE 13

|  | This Example | Example 1 |
|---|---|---|
| 2,2 DNP selectivity | 6.6 | 1.4 |
| Acetic acid formed | 0.46 | 0.24 |

These results demonstrate that 2,2 DNP selectivity can be influenced by packing the reactor. In addition, the amount of byproduct acetic acid is also increased.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process for the selective formation of 2-nitropropane and 2,2-dinitropropane, the process comprising:
    reacting propane with aqueous nitric acid at a pressure of at least about 1000 psi and a temperature of between about 215 and about 290 degrees Celsius; and
    recovering the formed nitrated compounds,
    wherein the aqueous nitric acid is a 10 to 50 weight percent solution.

2. A process according to claim 1 wherein the aqueous nitric acid is a 15 to 40weight percent solution.

3. A process according to claim 1 wherein the aqueous nitric acid is a 18 to 35weight percent solution.

4. A process according to claim 1 wherein the molar ratio of propane to nitric acid is at least about 1.2 to 1.

5. A process according to claim 1 wherein the temperature is greater than 230degrees Celsius.

6. A process according to claim 1 wherein the reaction is conducted in a downflow configured reactor.

7. A process according to claim 6 wherein the reactor is surrounded by a shell for feeding heat exchange fluid to the outer surface of the reactor.

8. A process according to claim 1 wherein the reaction is conducted in a packed reactor.

9. A process according to claim 1 wherein the reaction is conducted in an un-packed reactor.

10. A process according to claim 1 wherein the weight ratio of 2-nitropropane to 2,2-dinitropropane is at least about 15:1.

* * * * *